United States Patent
Matsuzawa et al.

(10) Patent No.: US 7,991,115 B2
(45) Date of Patent: Aug. 2, 2011

(54) MEDICAL IMAGE DIAGNOSTIC DEVICE

(75) Inventors: Yohei Matsuzawa, Nasushiobara (JP); Makoto Nakano, Nasushiobara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 117 days.

(21) Appl. No.: 12/329,906

(22) Filed: Dec. 8, 2008

(65) Prior Publication Data

US 2009/0154647 A1 Jun. 18, 2009

(30) Foreign Application Priority Data

Dec. 12, 2007 (JP) .................. 2007-321196

(51) Int. Cl.
*G01N 23/04* (2006.01)
*H05G 1/00* (2006.01)
*H05G 1/08* (2006.01)
*G01T 1/00* (2006.01)

(52) U.S. Cl. .......... 378/63; 378/98; 378/98.3; 378/98.5; 378/165; 378/166; 250/394

(58) Field of Classification Search .............. 378/4–20, 378/62, 63, 98, 98.2, 98.3, 98.5, 165, 166, 378/210; 600/407, 425, 427, 431, 436; 250/302, 250/303, 362, 363.01, 363.03, 363.04, 370.08, 250/370.09, 393, 394

See application file for complete search history.

(56) References Cited

U.S. PATENT DOCUMENTS

| 6,303,935 | B1* | 10/2001 | Engdahl et al. | 250/363.03 |
| 6,490,476 | B1* | 12/2002 | Townsend et al. | 600/427 |
| 6,631,284 | B2* | 10/2003 | Nutt et al. | 600/427 |
| 6,961,606 | B2* | 11/2005 | DeSilets et al. | 600/415 |
| 7,652,256 | B2* | 1/2010 | Lusser | 250/363.05 |
| 2004/0030246 | A1* | 2/2004 | Townsend et al. | 600/427 |
| 2005/0207530 | A1* | 9/2005 | Inoue et al. | 378/63 |
| 2006/0078183 | A1* | 4/2006 | deCharms | 382/128 |
| 2007/0100225 | A1* | 5/2007 | Maschke | 600/407 |
| 2007/0189456 | A1* | 8/2007 | Haras | 378/98.5 |

FOREIGN PATENT DOCUMENTS

| JP | 4-246328 | 9/1992 |
| JP | 2002-102203 | 4/2002 |
| JP | 2002-336212 | 11/2002 |

* cited by examiner

*Primary Examiner* — Anastasia Midkiff
(74) *Attorney, Agent, or Firm* — Oblon, Spivak, McClelland, Maier & Neustadt, L.L.P.

(57) ABSTRACT

In a medical image diagnostic device, wherein X-Ray CT devices and PET devices are longitudinally disposed, and which has a tubular imaging part for positioning a subject who is placed on the top surface of a bed and collecting image data, an illumination part is provided for producing a suitable level of brightness to the display part, which is for providing information to the subject without having to adopt every imaging position within the tubular imaging part, and to the imaging part.

6 Claims, 6 Drawing Sheets

MEDICAL IMAGE DIAGNOSTIC DEVICE

BACKGROUND OF THE INVENTION

1. Field of the Invention

The present invention relates to a medical image diagnostic device that comprises a combination of an X-ray CT device and a nuclear medical diagnostic device (for example, a PET device).

2. Description of the Related Art

Advances in medical image diagnostic devices have been remarkable, and they are used for early-stage discovery of diseases, confirmation of the location and shape/size of lesions, and the monitoring of treatment progress, thus contributing to the improvement of medical welfare. There are many types of these medical image diagnostic devices used, for example X-ray diagnostic devices, ultrasound diagnostic devices X-ray CT devices, magnetic resonance imaging devices, nuclear medical diagnostic devices, etc., according to the diagnostic objectives.

Each of these medical image diagnostic devices has, respectively, different functional characteristics, and in recent times, by obtaining diagnostic images of the same patient (subject) through multiple medical image diagnostic devices, more definite diagnoses are being performed. For example, comprehensive observation is being performed of internal morphological information, obtained as cross-sectional images and three-dimensional images by means of an X-ray CT device, and information about human tissue physiological functions and biochemical metabolic functions, obtained through imaging the dose distribution of radioactive isotopes by means of a nuclear medical diagnostic device.

In this case, X-ray CT devices and nuclear medical diagnostic devices, even if they are within the same medical facility, are normally placed in separate imaging rooms, and imaging requires subjects to be moved between the respective imaging rooms, placing a heavy burden on the subjects. Also, regarding subjects with limited mobility, members of the medical staff have to place them on gurneys and transport them in that state to the respective imaging rooms, so one cannot ignore the burden on medical staff.

Thus, while reducing such burdens on the subject and medical staff, various complex devices have been suggested wherein, in order to raise the diagnostic effectiveness, X-ray CT device pedestals and nuclear medical diagnostic device pedestals are arranged and placed within the same imaging room, and regarding the subject, who lies on the top surface of a shared imaging bed, it has become possible to carry out imaging, in order and consecutively, by means of an X-ray CT device and a nuclear medical diagnostic device (see Japanese published unexamined application publication number 2005-348841).

The complex devices described in Japanese publication number 2005-348841 are configured respectively as independent X-ray CT device pedestals and nuclear medical diagnostic device pedestals, but recently, there have been proposals to house the imaging part of an X-ray CT device and the imaging part of a PET device in one pedestal.

Incidentally, with X-ray CT devices and PET devices, the subject is made to lie on the top surface of the bed, and sent into the imaging part, which is formed in the shape of a hollow tube (dome-shaped), following which image data is collected, but with medical image diagnostic devices that are configured as a single unit combining an X-ray CT device and a PET device, the length (depth) of the imaging part for positioning the subject and collecting image data increases. In particular, current X-ray CT devices have become capable, for example, of simultaneously imaging 256 slices, incorporating multiple rows of sensors, and for this reason the length of the imaging part has increased dramatically, while the length has also increased of the imaging part of the hollow tube formed between the front cover and rear cover of medical image diagnostic device pedestals that are configured as a single unit combining an X-ray CT device and a PET device.

With the increase in the length of the imaging part of the hollow tube, it was difficult for illumination light from the exterior (in other words, from within the imaging room) to enter this location, so the interior of the imaging part turned out dark, and it was difficult to adequately brighten the interior of the imaging part, even if the illumination of the imaging room was brightened. Also, between the imaging start point and reaching the completion point, this dark imaging part accounts for a large portion of the subject's field of vision, and so there was the problem of causing significant distress to the subject. Furthermore, for the collection of image data by means of a PET device (hereafter, "PET imaging"), usually the time taken is around 30 minutes, and during this time, the subject must remain still, lying within the imaging part, thereby imparting distress and a sense of being enclosed.

In addition, with conventional X-ray CT devices, in the edges of the imaging part, namely the covers of the pedestal's front surface and rear surface, a display mechanism is provided. Thus, the subject viewing this display is able to be aware of the progress of the imaging, the start and stop of holding the breath, the continuous time that the breath is held, etc., but with a medical image diagnostic device pedestal that is a single unit combining an X-ray CT device and a PET device, the length of the imaging part is dramatically longer, and from within the imaging part, the display mechanism located in the edges cannot be viewed. Hence, disadvantageously, from both the perspective of the person performing the imaging and the perspective of the subject, the display mechanism's functions cannot be adequately utilized.

SUMMARY OF THE INVENTION

An aspect of the present invention is a medical image diagnostic device having a tubular space for inserting a subject into its interior, and imaging it. This medical image diagnostic device comprises: an X-ray imaging detector configured to detect X-rays emitted from said object, and disposed at locations along the direction of the circumference, which are areas in the longitudinal direction of said tubular space and represent a cross-section of said tubular space; a radiation detector configured to detect radiation emitted from said object, and disposed at locations along the direction of the circumference, which are areas different from said X-ray imaging detector of said tubular space and represent a cross-section of said tubular space and; a light emitting part configured to form a display part that shows information intended for said object or an illumination part that illuminates said tubular space, said light emitting part being disposed at locations that set the light emission range to be the exteriors of said X-ray imaging detector and said radiation detector, and that are areas in the longitudinal direction of said tubular space.

According to an aspect of the present invention, the interior of the imaging part is brightened and information about the progress of the imaging, etc. is provided for the subject placed within the imaging part with the field of vision being narrowly restricted. It results in freeing the subjects from the feeling of being enclosed, and getting them to undergo the imaging of medical images with a sense of reassurance, and thus a medical image diagnostic device that takes into account the standpoint of the subject is provided.

Moreover, because the imaging part of the X-ray CT device and the PET device is shared, and it is possible to sequentially align the subject, who is placed on the top surface of the bed, to each imaging position of the X-ray CT device and PET device, it is hence possible to efficiently perform CT imaging and PET imaging, thus reducing the burden on the subject and medical staff.

Moreover, because an illumination part and/or display part is provided, to avoid every imaging position by the X-ray CT device and the PET device, it is possible to definitely prevent causing any hindrance to the collection of image data using both devices.

Moreover, by utilizing the wall surfaces of the imaging part for a screen, including every position with the X-ray CT device and PET device, any hindrance to the collection of image data using both devices are prevented, broadening the range of the display.

Moreover, instructions can easily be given to the subjects to start and stop holding their breath, and imaging failures can be prevented. Moreover, it is possible to inform the subject of the time remaining until the end of the imaging, thus providing a sense of reassurance. Furthermore, by showing videos such as short films, even if the imaging takes a long time, subjects will not become bored, and it will be possible to get them to undergo imaging in a more relaxed manner.

Moreover, the illumination does not directly enter the eyes of the subject, there is no glare, and even with imaging that takes a long time, the subject can be kept still.

DETAILED DESCRIPTION OF THE PREFERRED EMBODIMENTS

The following is an explanation of one embodiment of the medical image diagnostic device according to the present invention.

Additionally, in these diagrams, the same parts have been marked with the same symbols.

Figure 1:
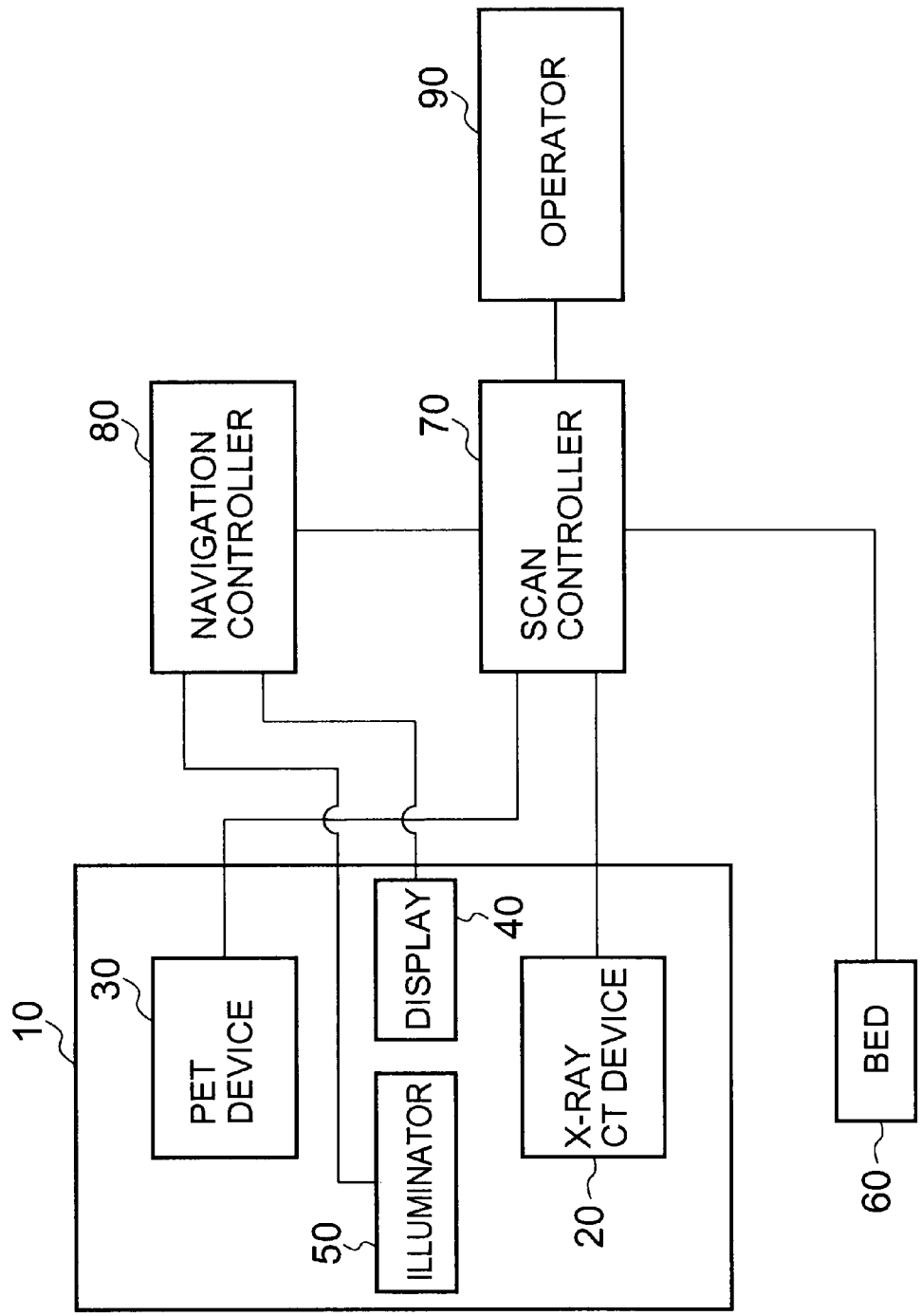
FIG. 1 is a schematic diagram showing the overall structure of one embodiment of the medical image diagnostic device.

FIG. 1 is a schematic diagram showing the overall structure of one embodiment of a medical image diagnostic device. The medical image diagnostic device main unit 10 comprises an X-ray CT device 20 and a PET device 30, sharing a pedestal. The medical image diagnostic device main unit 10, which will be described again later, comprises an imaging part shared by an X-ray CT device 20 and a PET device 30, in which a display part 40 and an illumination part 50 are provided. Additionally, the medical image diagnostic device comprises a bed device 60, for sending a subject into the imaging part. Furthermore, it also comprises, among others, a scan controller 70, for controlling the X-ray CT device 20, the PET device 30 and the bed device 60, and it comprises a navigation controller 80, which controls the display part 40 and the illumination part 50 under the control of this scan controller 70, and it comprises an operator 90, with which an operator enters the relevant instructions and settings into the scan controller 70.

Figure 2:
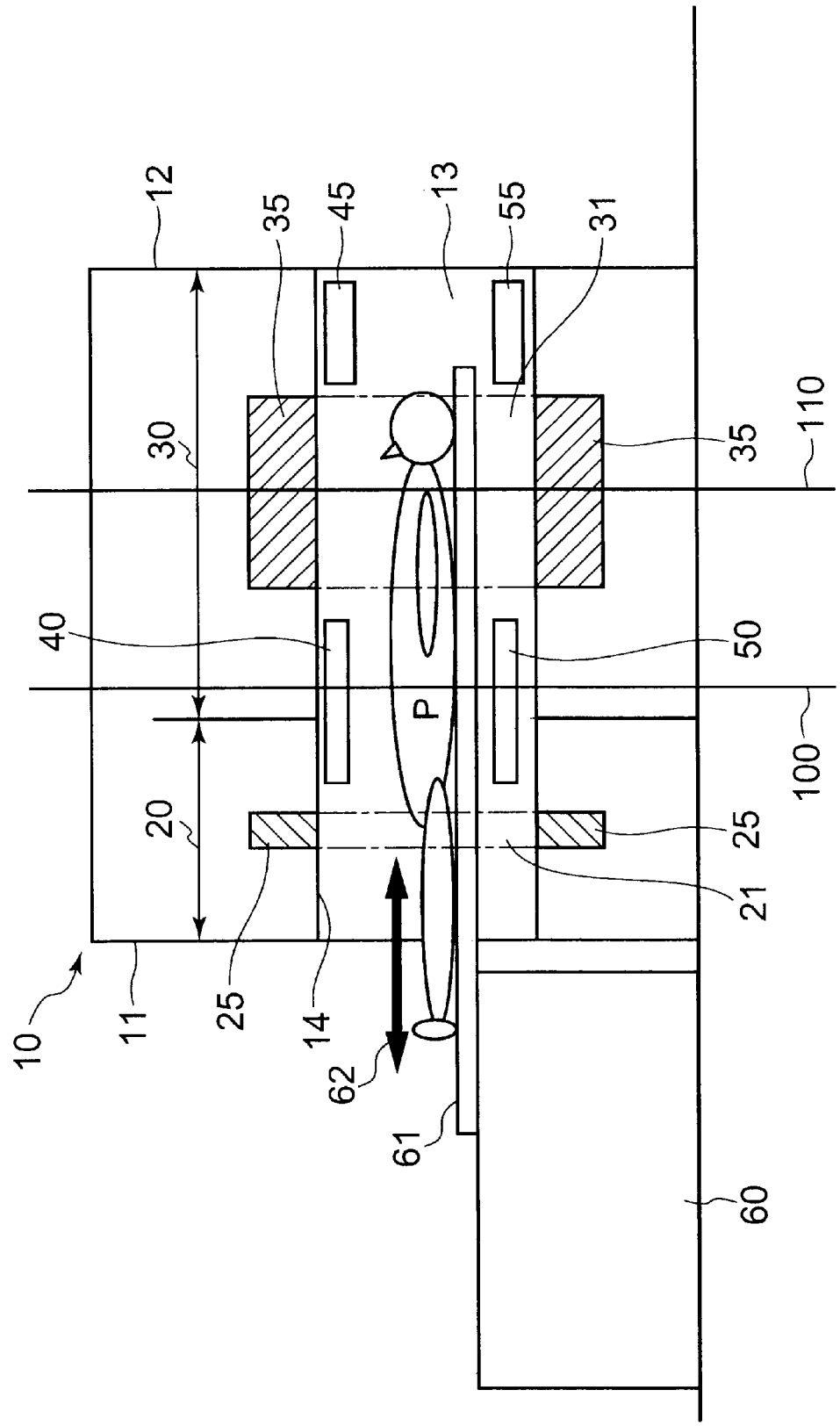
FIG. 2 is a longitudinal cross-section diagram, viewed from the side of one embodiment of the medical image diagnostic device.

Next, referring to FIG. 2, a more detailed structure of one embodiment of the medical image diagnostic device according to the present invention is explained.

FIG. 2 is a longitudinal cross-section diagram viewed from the side of one embodiment of the medical image diagnostic device according to the present invention. FIG. 2 diagrammatically shows the relationship between the locations of the X-ray CT device 20 and the PET device 30, which are placed in the interior of the medical image diagnostic device main unit 10, and the relationship with an imaging part 13.

The medical image diagnostic device main unit 10 is installed on the floor, and in its interior, the X-ray device 20 and the PET device 30 share the imaging part 13, and are placed in-line in the longitudinal direction. The surface of the medical image diagnostic device unit 10 is covered by covers, so that, passing between a front cover 11 and a rear cover 12, the imaging part 13 of a hollow tube is formed in an almost central part of the medical image diagnostic device unit 10. Into this imaging part 13, a top surface 61 of a bed 60, on which a subject P is placed, is inserted so as to freely move from the exterior of front cover 11, as shown by arrow 62. Furthermore, imaging part 13 is formed in a hollow tube surrounded by a cover 14 (hereafter referred to as a dome cover) made of a material such as mylar, and by means of this dome cover 14, the interior of the medical image diagnostic device unit 10 and the imaging part 13 are segmented.

The medical image diagnostic device unit 10 is divided into the X-ray CT device 20 and the PET device 30. In FIG. 2, the bed 60 is placed on the left side, and the X-ray CT device 20 and the PET device 30 are lined up in sequence. As a result of such an arrangement, the subject P is sent in from the bed 60, and undergoes imaging by the X-ray CT device 20, and subsequently undergoes imaging by the PET device 30.

In FIG. 2, the rear cover 12 side is the head side, and the front cover 11 side is the feet side, so in this case, when undergoing imaging by the PET device 30, the subject P will view mainly the screen of the display part 45. On the other hand, sometimes the subject P enters, in the opposite direction. In this case, when undergoing imaging by the PET device 30, the display part 40 is closer to the head, so the subject P will view the screen of display part 40. Accordingly, the navigation controller 80 determines and issues instructions, regarding whether to display on the screen of display part 40, or to display on the screen of display part 45, according to the direction in which the subject P is facing. Regarding the direction in which the subject P is facing, instructions may be issued from the operator 90, or the navigation controller 80 may make the determination from the progress of the examination.

Alternatively, regardless of the direction in which the subject P is facing, display may be carried out on the screens of both the display part 40 and the display part 45.

The X-ray CT device 20 is provided, in the shaded portion, with an X-ray part 25, consisting of an X-ray tube revolving around imaging part 13, and X-ray detectors, the scope of the shape indicated by the symbol 21 is the location at which the irradiation and detection of X-rays is performed, and X-ray part 25 is rotated.

Hereafter, this location 21 is referred to as the CT imaging location 21. This CT imaging location 21 and the X-ray part 25 are located in the central area of X-ray CT device 25. Furthermore, this X-ray CT device 25 is located just inside the medical image diagnostic device unit 10, seen from the direction of progress 62 from the bed 60.

On the other hand, with the PET device 30, the scope of the shape indicated by the symbol 31 is the location at which gamma rays emitted from the subject P are detected, based on the radioactive dye administered in advance to the subject P, and in the shaded portion of this location 31, the PET detection part 35, which contains detectors that detect gamma rays, is arranged to surround the periphery of the imaging part 13. Hereafter, this location 31 is referred to as the PET imaging location 31. This PET imaging location 31 and the PET detection part 35 are located in the central area of PET device 30.

Furthermore, this PET device 30 is located just inside the medical image diagnostic device unit 20, seen from the direction of progress 62 from the bed 60.

Furthermore, with the dome cover 14 provided on the interior peripheral surface, only the CT imaging location 21 and the PET imaging location 31 portions are colored and patterned differently from the rest, and the CT imaging location 21 and the PET imaging location 31 can be visually checked from within the imaging part 31 by the subject P or medical staff.

Moreover, in the imaging part 13, in an attempt to avoid the CT imaging location 21 and the PET imaging location 31, the display parts 40 and 45 and the illumination parts 50 and 55 are provided. In other words, the display part 40 and the illumination part 50 are provided between the CT imaging location 21 and the PET imaging location 31. The display part 40 and the illumination part 50 are arranged to straddle the X-ray CT device 20 and the PET device 30.

The display part 40 is arranged at the lower portion of the top wall, along the top wall. The illumination part 50 is arranged so that it is mounted on the lower wall, along the lower wall of the internal dome of the medical image diagnostic device unit 10

On the other hand, the display part 45 and the illumination part 55 are provided appropriately in the space from the CT imaging location 21 to near the front cover 11, or in the space from the PET imaging location 31 to near the rear cover 12. The display part 45 is placed, along the upper wall of the interior dome of the medical image diagnostic device unit 10, in this lower portion of the upper wall. The illumination part 55 is mounted and placed, along the lower wall of the interior dome of the medical image diagnostic device unit 10, in this lower wall.

Incidentally, the display part 40 is intended to provide information, such as the progress of imaging, to the subject P, and to reduce the distress of the subject P during imaging, or it may be provided for the medical staff performing the imaging to issue instructions to the subject to hold the breath, or to tell the subject to stop holding the breath. For example it displays the fact that imaging is currently being performed using the current X-ray CT device 20, or the fact that imaging is in progress using the PET device 30, and it displays the remaining time until imaging is completed, etc, during imaging using the PET device 30, which requires a relatively long time. In addition, videos such as short films, etc. may be displayed, and by selectively displaying videos to suit the subject's preferences, relaxation can be provided to the subject who is undergoing imaging.

For this display part 40, various types of well-known display devices may be used, for example an EL display, an LCD display or an electronic ink sheet. Moreover, regarding its shape also, it is possible to use appropriate types, such as flat-screen, curved screen to fit the wall surface of the tubular dome cover 14, etc. In addition, the surface of the dome cover 14 of the imaging part 13 can also be used as a screen, and in this case, a projector is positioned on the exterior of front cover 11 or rear cover 12, and it can be made to project any necessary information from the exterior of imaging part 13 to the interior of imaging part 13, and to display it on the surface of cover 14. Moreover, for the display part 45 also, the same kind of objects as with display part 40 can be used.

Furthermore, in FIG. 2, the display part 40 is shown as being provided at two locations, but without such limitation, it may be provided at one location, or three locations or more.

On the other hand, regarding the illumination part 50, if the length of the imaging part 13 is as much as 1 meter, it is difficult for light from the exterior to enter, and because the imaging part 13 is dark, this is related to the subject P feeling unease and a sense of being enclosed, etc., so it is provided in order to reduce this unease and sense of being enclosed. For this reason, the imaging part 13 is given a reasonable amount of lighting, while ensuring that the subject P does not feel the glare, for example, where there is indirect lighting, such as when the light leaks from the bottom of the top surface 61, which is where the subject has been inserted, to the imaging part 13. It is preferable for this illumination part 50 to be an adjustable light, in which the brightness can be adjusted appropriately.

Moreover, the illumination part 50 also may be provided in a distributed manner to multiple locations, not just one location, and it may also be provided so as to be at a higher location than top surface 61. Also, the illumination part 50 is provided so that it is divided into the X-ray CT device 20 side and the PET device 30 side, and during CT imaging with the X-ray CT device 20, the X-ray CT device 20 side's illumination part 50 lights up, while during PET imaging with the PET device 30, the PET device 30 side's illumination part 50 lights up. In this way, the subject P can easily be made aware of whether imaging is in progress at CT imaging location 21, or whether imaging is in progress at CT imaging location 31, and the illumination part 50 may be used as a function of the display part 40.

Conversely, when various kinds of information are displayed on the display part 40, the screen of the display part 40 also brightens the interior of the imaging part 13, so if the display part 40 is activated, the lighting of the illumination part 50 can be stopped or restricted in brightness, with the aim of energy conservation. It is also possible to omit placement of the illumination part 50. The above explains illumination part 50, but the same kind of objects can be used for illumination part 55 as well.

FIG. 2 shows subject P progressing in a horizontal direction through the medical image diagnostic device unit 10, but a cross section viewed from a radial direction is also described below. As a radial view diagram, the surface on cross-section 100 includes the display part 40 and the illumination part 50, and the surface on cross-section 110 includes the PET detection part 35, which are described below.

Regarding the Arrangement of All Parts

As described above, the display parts 40 and 45, and the illumination parts 50 and 55, are arranged in the interior of the medical image diagnostic device 10, and the issuing of instructions to the subject P, and the brightening of the interior have been explained.

But for each of those parts, it does not mean that they can be placed anywhere for the sake of brightening the interior. Along with aiming to reduce the unease of the subject P, it is desirable to arrange them such that no problems arise in imaging. Hence, the arrangement of the display parts 40 and 45, and the illumination parts 50 and 55 is described next.

Figure 3A:
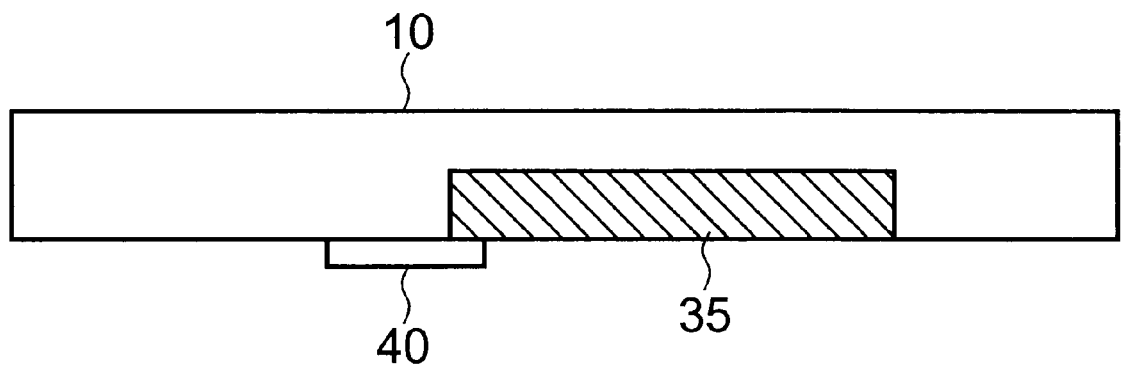
FIG. 3A is one example in which the display part is positioned in the interior.

FIG. 3A is one example in which the display part 40 is arranged within the interior. Along with the arrangement of the display part 40 on the upper part of the dome, it shows the case where the PET detection part 35 overlaps the location of the display part 40, against the progress direction of the subject P. With this kind of arrangement, by arranging the display part 40 between the PET detection part 35 and the subject P, in addition to the display part 40 being an obstruction, a problem arises in that the light generated from the display part 40 ends up entering the PET detection part 35. The PET detection part 35 is weak against illumination of light, and for that reason, there is the problem that in detection, noise arises, failure occurs, etc. Accordingly, as shown in FIG. 3A, it is desirable to avoid arrangements in which noise arises due to the display part 40.

Figure 3B:
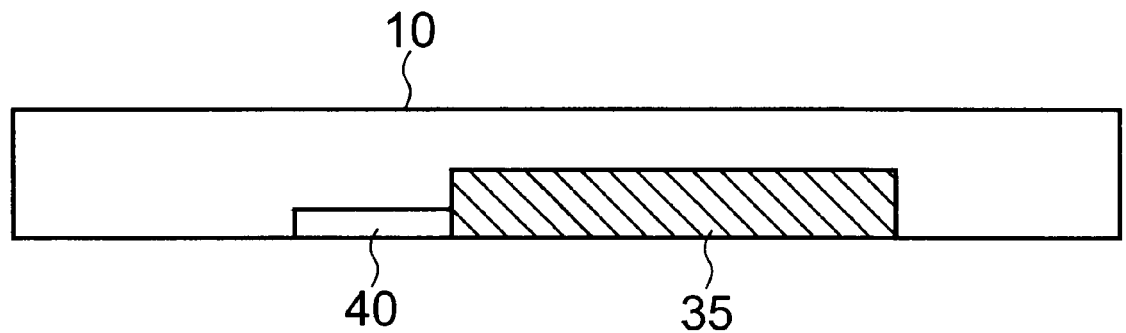
FIG. 3B is another example in which the display part is positioned in the interior.

FIG. 3B is another example in which the display part 40 is arranged within the interior. In this case, along with the display part 40 being arranged in the inner wall of the dome, it is arranged such that it is aligned with the PET detection part 35. Because it is aligned with the PET detection part 35, it is possible to avoid having the display part 40 come in between and cause a failure, but since they are adjacent, there is the problem that the light from the display part 40 enters the PET detection part 35.

The above problems arise for nuclear medical diagnostic devices, which detect radiation and perform diagnoses, but in the case of devices that perform detection using magnetism, for example, MRI devices, these problems do not really arise. Accordingly, MRI devices, for example, similarly have the problem of the lengthening of the dome interior, but if one were to illuminate the interior in such MRI devices, there will be, as shown in FIG. 3A, arrangements on the lower part of the detectors, and as shown in FIG. 3B, arrangements in alignment. At least, there is no need to consider the arrangements of the display part 40 and 45, and the illumination part 50 and 55.

In the following embodiments, from the fact that by connecting the X-ray CT device 20 and the PET device 30, the interior of the dome becomes larger and darker, thus is intended to be displayed and illuminated. In addition, unlike MRI devices, PET devices are characteristically sensitive to light, and as described below, the arrangements of the display part 40 and 45, and the illumination part 50 and 55 have been devised.

FIGS. 3A and 3B were explained using the display part 40, but with respect to the point that the display light gives rise to noise, the display part 45 is similar, and moreover, it is desirable that, with respect to the point that light is generated, the illumination part 50 and 55 are arranged with similar considerations. Hence, regarding arrangements for resolving the abovementioned problems, we will explain in further detail, relating to the structure of FIG. 2.

Embodiments Related to the Arrangements of All Parts

Figure 4:
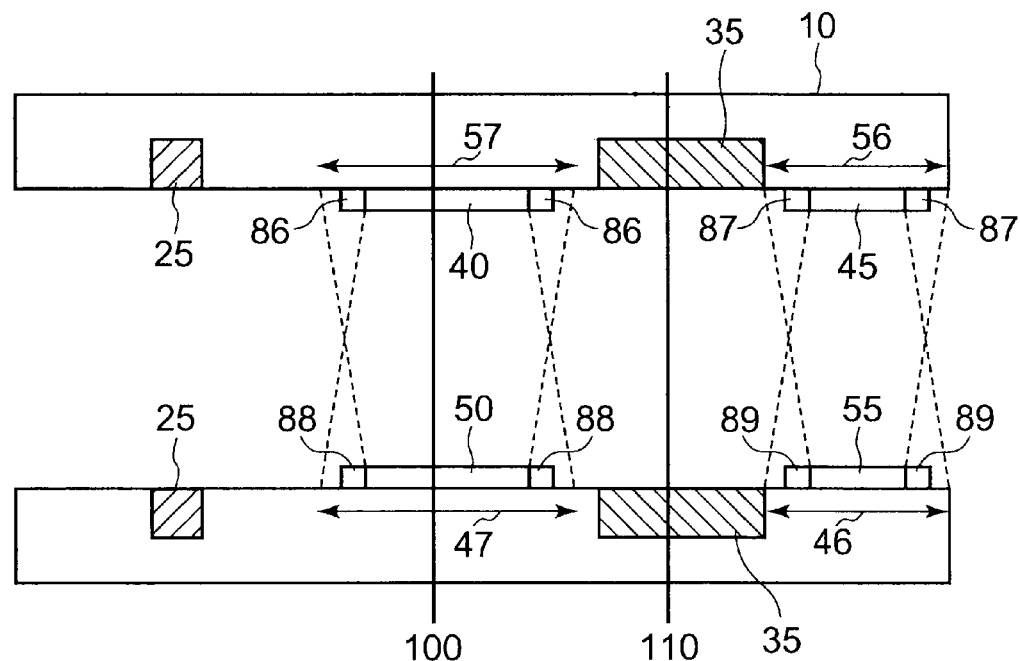
FIG. 4 is a block diagram explaining the placement within the dome of the medical image diagnostic device.

FIG. 4 is a block diagram explaining the arrangement within the dome of the medical image diagnostic device. The structure of FIG. 4 is basically the same as that of FIG. 2, but the arrangement of the display parts 40 and 45 and the illumination parts 50 and 55 are explained in further detail. As explained in relation to FIGS. 3A and 3B, the display parts 40 and 45 are arranged on the lower side of the inner wall of the upper part of the dome upper part, and are separated from the PET detection part 35. In the same way, the illumination parts 50 and 55 are arranged on the upper side of the inner wall of the upper part of the dome, and are separated from the PET detection part 35.

When each part is arranged to be separated from the PET detection part 35, close position to PET detection part 35 will cause light to enter. Taking into consideration the interior space allocation, arrangements involving too much separation are also difficult. Hence the illumination scopes of the display part 40 and 45, and the illumination part 50 and 55 are set as the exterior of the PET detection part 35. In other words, according to the arrangement in FIG. 4, the display part 40 and 45, and the illumination part 50 and 55 are arranged at a location in which the exterior of the PET detection part 35 and the X-ray part 25 are set as the light illumination scope.

Consequently, because the PET detection part 35 is not illuminated by light, it is possible to avoid noise from the incidence of light.

The display part 40 and the illumination part 50 are arranged in between the X-ray part 25 and the PET detection part 35, so as not to overlap either the X-ray part 25 or the PET detection part 35, being arranged further from a location overlapping the X-ray part 25 and the PET detection part 35 to set the illumination scope of the light generated from the display part 40 and the illumination part 50 respectively within the space between the X-ray part 25 and the PET detection part 35.

The display part 45 and the illumination part 55 are arranged from the PET detection part 35 to the side of the rear cover 12, so as not to overlap the PET detection part 35, being arranged further from a location overlapping the X-ray part 25 and the PET detection part 35 to set the illumination scope of the light generated from the display part 45 and the illumination part 55 respectively within the space between the PET detection part 35 and the exterior.

The display part 40 is the upper part of the dome of the medical image diagnostic device 10, and its illumination scope 47 is arranged at a location that is the exterior of the PET detection part (lower). In this case, the location of the display part 40 is separated from the PET detection part 35 (upper). When the display part 40 displays information, it generates light, so that light reaches the illumination scope 47 of the lower part of the dome. In order that this illumination scope 47 does not overlap the X-ray part 25 and the PET detection part 35, this illumination scope 47 is formed on the exterior of the PET detection part 35. Because the illumination scope 47 is formed on the exterior of the PET detection part 35, there is no incidence of light into the PET detection part 35.

Also, the display part 45 is similar to the display part 40. The display part 45 is arranged at the upper part of the dome so as to emit light at a position where the illumination scope 46 is the exterior of the PET detection part 35, so the illumination scope 46 is formed on the lower part of the dome. As this illumination scope 46 is set to be the exterior of the PET detection part 35, there is no incidence of light into the PET detection part 35.

Similarly, the illumination part 50 is arranged at the lower part of the dome to emit light at a position where the illumination scope 57 is the exterior of the PET detection part 35, thus the illumination scope 57 is formed on the upper part of the dome. On the other hand, the illumination part 55 is also arranged at the lower part of the dome to emit light at a position where the illumination scope 56 is the exterior of the PET detection part 35, thus the illumination scope 56 is formed on the upper part of the dome. The illumination scope 56 and 57 are set to be the exterior of the PET detection part 35 and there is no incidence of light into the PET detection part 35.

Shield

As described above, according to the arrangement of all parts, the illumination scope is set to be the exterior of the X-ray part 25 and the PET detection part 35, but other configurations to avoid light incident into the PET detection part 35 are conceivable. For example, it is conceivable to arrange a shield 86 on the side of the display part 40. Arranging the shield 86 makes the light illumination scope 47 narrower. This narrowed illumination scope 47 is set to be between the X-ray part 25 and the PET detection part 35. Because the illumination scope 47 is narrowed, the display part 40 becomes easier to arrange between the X-ray part 25 and the PET detection part 35, and for example, it is also possible to arrange it closer to the X-ray part 25 or closer to the PET detection part 35. As the degree of freedom in arranging the display part 40 increases, it becomes possible to arrange the display part 40 where the subject P can easily view it.

Herein, the shield 86 is arranged so as to cover the display part 40 on the sides along the direction of progress and backward direction of the subject P. Seen from the cross-section of the dome, when the display part 40 is arranged within the dome along the radius direction in a curved line, this shield 86 is also arranged along the radius direction in a curved line. The display part 40 may not be in a curved line but in a plane, and in this case, the shield 86 is also arranged along the plane of the display part 40 in a linear fashion.

However, because the inner wall of the dome is curved, in order not to leak light from the gap of the shield 86, the shield 86 seals the display part 40 until reaching the inner wall of the dome. In such a manner, arranging the shield 86 on the sides seals light so that it does not leak to the exterior. Sealing light with the shield 86 restrains the spreading of light from the display part 40 within a certain scope and minimizes the size of the illumination scope 47, thereby preventing light from illuminating the PET detection part 35.

Although the shield 86 is arranged on the display part 40, a shield 87 can also be arranged on the display part 45, a shield 88 can be disposed on the illumination part 50, and a shield 89 can be disposed on the illumination part 55. This narrows the illumination scopes 46, 57 and 56 respectively, thereby preventing light from illuminating the PET detection part 35. The arrangement of the shields 87, 88, 89 is the same as that of the shield 86.

Also, as described above, because the light illumination scope from each part is narrowed, the degree of freedom to arrange the display part 40, 45 increases, and accordingly it is suitable to arrange it at a position easily viewable from the subject P. Therefore, the display part 40, 45 are arranged as shown in FIG. 4. Hence, when progressing in the rear cover 12 direction, specifically, in the rightward direction in FIG. 4, the subject P can view display part 45 arranged on the rear cover 12 side away from the PET detection part 35. In other words, the display part 45 is positioned in front of the face of the subject P and the subject P can view the screen of the display part 45. On the other hand, when progressing in the front cover 11 direction, specifically in the leftward direction in FIG. 4, the subject P can view the display part 40 arranged on the front cover 11 side away from the PET detection part 35. In other words, the display part 40 is positioned in front of the face of the subject P and the subject P can view the screen of the display part 40.

Figure 5:
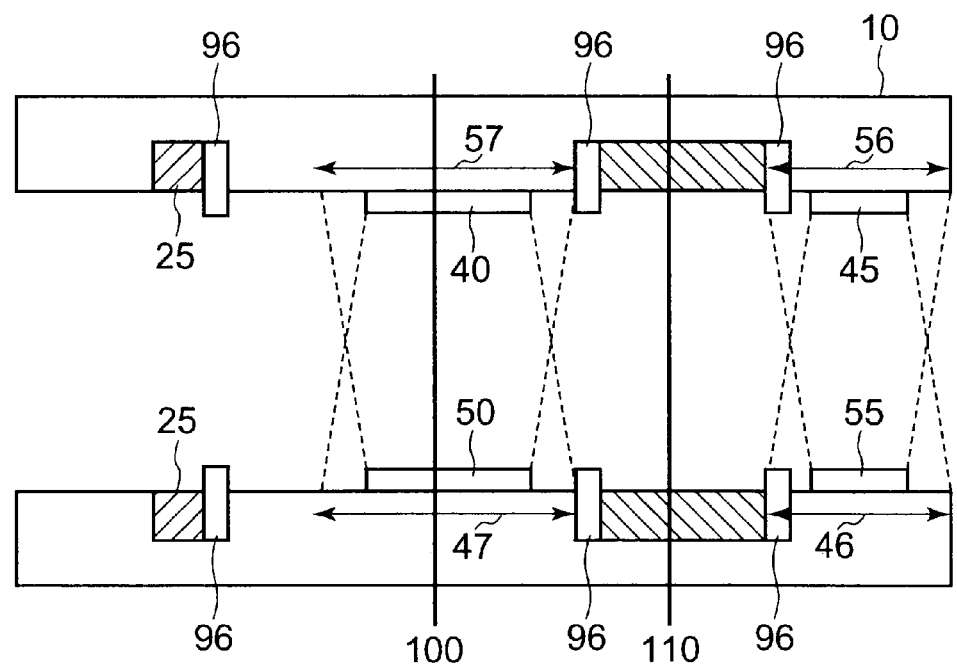
FIG. 5 is a block diagram explaining another example of the placement within the dome of the medical image diagnostic device.

FIG. 5 is a block diagram showing another example of the arrangement in the dome of the medical image diagnostic device. As with FIG. 4, FIG. 5 also describes the arrangement of the display part 40, 45 and the illumination part 50, 55, instead of the shields 86-89 that are provided in FIG. 4, shields 96 are provided to shield light from the PET detection part 35 in FIG. 5. These shields 96 shield light from the display part 40, 45 and the illumination part 50, 55. In FIG. 5, the shields 86-89 are not arranged, but those may be arranged along with the shields 96. The use of both configurations of FIG. 4 and FIG. 5 allow more assured prevention of the incidence of light into the PET detection part 35. However, in FIG. 5, for the purpose of clarity in explanation, the case where shields 96 are used is described. Furthermore, as another example, in FIG. 9, a case where covers 130 are used will be described later, but this can also be used complementarily.

The shield 96 is arranged in the circumference direction along the X-ray part 25 and the PET detection part 35, and covers the X-ray part 25 and the PET detection part 35 in the direction of progress of the subject P, and backward. The X-ray part 25 and the PET detection part 35 are arranged in the dome of the medical image diagnostic device 10, along the circumference direction forming a cross-section.

Therefore, arranging the shield 96 along the circumference direction of this dome cross-section shields light from the X-ray part 25 and the PET detection part 35. In this case, the shield 96 may be simply formed on the sides of the X-ray part 25 and the PET detection part 35, but also, as shown in FIG. 5, it may be formed so as to protrude into the dome. Protruding into the dome allows the shielding of light by the height of the protrusion.

It should be noted that this shield 96 is arranged on both sides of the PET detection part 35 in the direction of progress of the subject P and the backward direction. Arranging shields 96 on both sides shields light from the display part 40 and the illumination part 50 on the X-ray part 25 side of the shield 96, while shielding light from the display part 45 and the illumination part 55 on the rear cover 12 side of the shield 96. On the X-ray part 25, it is enough for the shield 96 to be arranged only on the PET detection part 35 side, because a light-emitting device is not arranged on the exterior of the X-ray part 25.

In such a manner, arranging the shield 96 allows light from the display part 40, 45 and the illumination part 50, 55 to illuminate the sides of the shield 96, while preventing light from illuminating the X-ray part 25 and the PET detection part 35. In other words, even if the X-ray part 25 or the PET detection part 35 is within the light illumination scope without the shield 96, the shield 96 sets illumination scopes 46, 47, 56, 57 to be the exterior of the X-ray part 25 and the PET detection part 35. The shield 96 sets the scope, which is the exterior of the X-ray part 25 and the PET detection part 35, to be relatively wider with respect to the light illumination scope, thereby increasing the degree of freedom to arrange the display part 40, 45 and the illumination part 50, 55.

Figure 6:
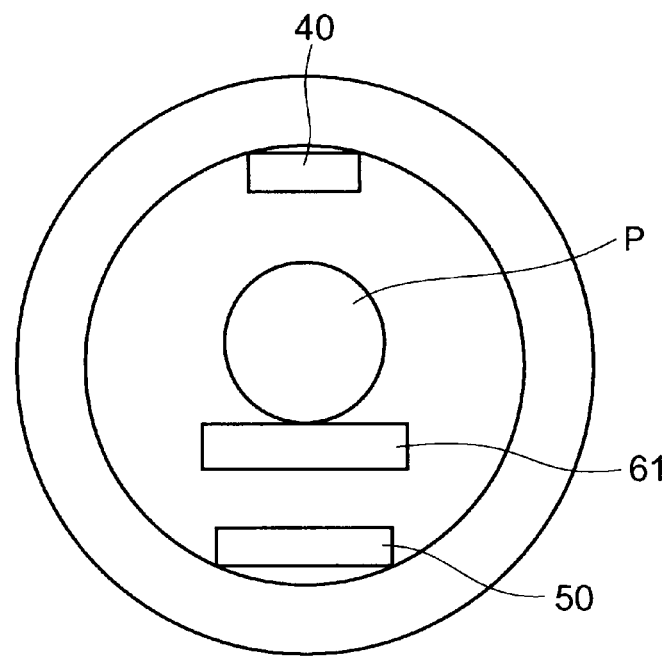
FIG. 6 is a cross-section diagram of the medical image diagnostic device.

FIG. 6 is a cross-section view of the medical image diagnostic device. In particular, FIG. 6 shows the cross-section along the cross-section 100 shown in FIG. 4. The cross-section 100 comprises the display part 40 and the illumination part 50 but not the X-ray part 25 and the PET detection part 35. Therefore, FIG. 6 shows a cross-section indicating the region illuminated with light. In the middle of FIG. 5, the subject P is lying on the top surface 61 and located in the center of the medical image diagnostic device 10. And, the display part 40 is arranged on the upper part and the illumination part 50 is disposed on the lower part of the dome where this subject P and the top surface 61 are incorporated. FIG. 6 is shown in such an arrangement that is along the cross-section 100, but when cutting along the cross-section including the display part 45 and the illumination part 55, the display part 40 in FIG. 6 is replaced with the display part 45 and the illumination part 50 is replaced with the illumination part 55.

Figure 7:
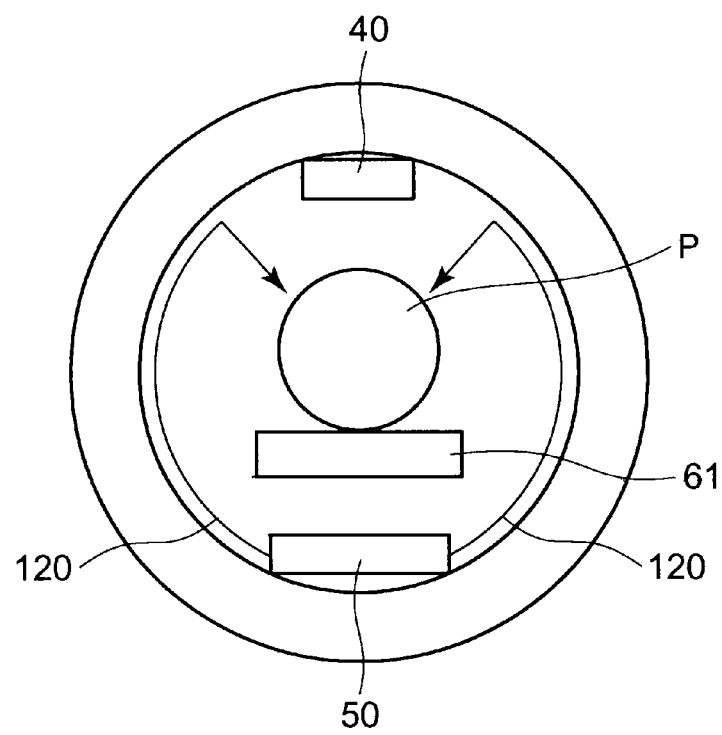
FIG. 7 is a cross-section diagram of the area including the lighting illumination circuit.

FIG. 7 is a cross-section view of a region including the light illumination paths. The region indicated by FIG. 7 is the same as that of FIG. 6. Because the subject P is oriented toward the display part 40 against the top surface 61, it results in an arrangement where the display part 40 is viewed directly. On the other hand, because the illumination part 50 is located on the rear side of the subject P, it does not result in viewing the illumination part 50 directly. However, light from the illumination part 50 is transmitted in the circumference direction within the dome and travels along the direction 120 toward the top of the dome. This allows the inside of the dome to be illuminated in the manner of indirect lighting, and thus, in that process, decreasing the intensity of light as well as lighting the inside entirely. This changes the inside of the dome, with its darkness and unease, into an environment where it is appropriately illuminated and comfortable. On the other hand, as described in FIG. 4 and FIG. 5, light into the X-ray part 25 and the PET detection part 35 sides is shielded, thereby preventing adverse effects on the devices.

Figure 8:
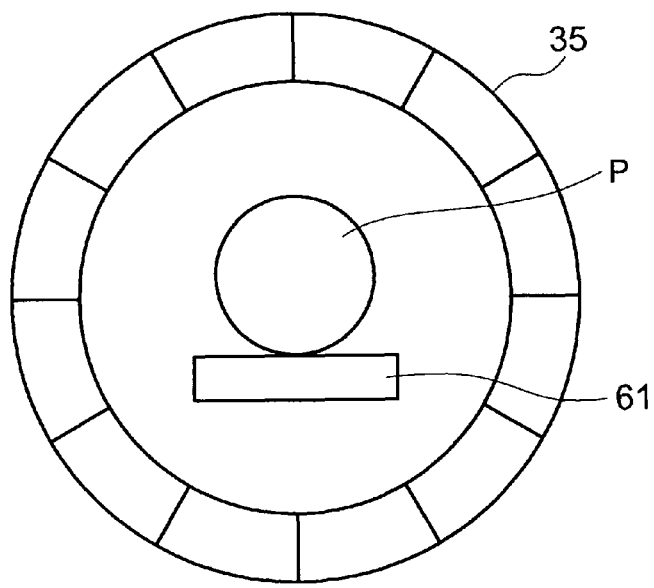
FIG. 8 is a cross-section diagram of the area in which the PET detection part is positioned.

FIG. 8 is a cross-section view of the region where the PET detection part is arranged. FIGS. 6 and 7 show the cross-section view of the medical image diagnostic device 10 along the cross-section 100, while FIG. 8 shows the cross-section along the cross-section 110.

The cross-section 110 comprises the PET detection part 35 but not the display part 40, 45 and illumination part 50, 55. Therefore, FIG. 8 shows the cross-section of a region to be detected by the PET device 30 but not illuminated with light. In the middle of FIG. 8, the subject P is laid on the top surface 61 and located in the center of the medical image diagnostic device 10. Moreover, the PET detection part 35 is arranged along the circumference direction of the dome where this subject P and the top surface 61 are incorporated. The cross-section 110 is the same at any location where the PET detection part 35 is included, the PET detection part 35 is disposed along the circumference, and the display part 40, 45 and the illumination part 50, 55 are not included.

Figure 9:
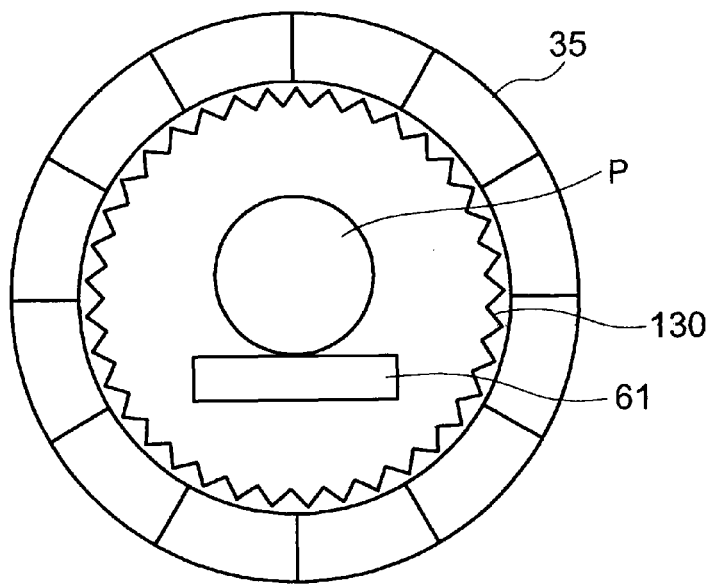
FIG. 9 is a cross-section diagram in which the PET detection part is covered with a cover.

FIG. 9 is a cross-section view in which the PET detection part is covered. The region indicated by FIG. 9 is the same as the one in FIG. 8. In FIG. 4 and FIG. 5, in order to prevent light incident into the PET detection part 35, shields 86-89 are disposed or a shield 96 is disposed, while in FIG. 9, a cover 130 is disposed. The cover 130 is disposed so as to cover along the circumference of the cross-section of the medical image diagnostic device 10. The cover 130 is layered over the surface of the PET detection part 35 but, in order not to leak light through the gap between the cover 130 and the PET detection part 35, the width of the cover 130 in the direction of progress and the backward direction with respect to the subject P may be made wider than that of the PET detection part 35. As a material for this cover 130, plastic is conceivable. The use of plastic allows shielding light from the display part 40, 45 and the illumination part 50, 55, while allowing radiation to be transmitted toward the PET detection part 35. Shielding light allows the prevention of noise and failure in the PET detection part 35, while transmitting radiation such as gamma rays allows performing imaging of the subject P. For the cover 130, any other materials that can shield the light as well as transmit radiation are conceivable but, on the contrary, metals are not suitable.

Now, the operation of an example of the medical image diagnostic device according to the present invention configured as described will be explained hereinafter.

The subject P to be imaged is laid on the top surface 61 of the bed device 60. Next, medical staff such as a physician or X-ray engineer enter the necessary instructions on imaging via the operator 90 to the scan controller 70. In response to this instruction, the scan controller 70 drives the bed device 60 and causes the top surface 61 where the subject P lies to be guided to the imaging part 13 of the medical image diagnostic device unit 10 and stopped at a predetermined place. Then, continuously under the instruction of the scan controller 70, for example, CT imaging by the X-ray CT device 20 would be started. It should be noted that, at this time, the navigation controller 80 causes the display part 40 or the illumination part 50 to be turned on in response to an operational signal from the scan controller 70.

In other words, during imaging by the X-ray CT device 20, the navigation controller 80 causes the display part 40 to display messages, for example, "CT imaging will be started" or "CT imaging has been completed". Also, in accordance with the timing of imaging, messages, for example, "please hold your breath", "please do not move for a while", "please exhale and relax" are displayed.

Therefore, the subject P waits for imaging to be completed in accordance with the instructions while viewing the display on this display part 40. It should be noted that the subject P can recognize the CT imaging location 21 by the part of the dome cover 14 surrounding the imaging part 13, which is identifiable by being partially colored. Also, if the illumination part 50 is provided separately on the X-ray CT device 20 side and the PET device 30 side, during imaging by the X-ray CT device 20, the navigation controller 80 causes the illumination part 50 on the X-ray CT device 20 to be turned on so that the subject P can recognize that the imaging is being currently performed by the X-ray CT device 20.

When imaging is completed by the X-ray CT device 20, the scan controller 70 drives the bed device 60 to cause the top surface 61 where the subject P lies to move toward the PET device 30 and stop at a predetermined place. At this time, if the illumination part 50 is provided separately on the X-ray CT device 20 side and the PET device 30 side, the navigation controller 80 causes the illumination part 50 on the X-ray CT device 20 side to be turned off, while causing the illumination part 50 on the PET device 30 side to be turned on. This allows the subject P to recognize that imaging has been switched from the X-ray CT device 20 to the PET device 30.

Also, in accordance with the control via the scan controller 70, the navigation controller 80 causes the necessary messages to be displayed on the display part 40. The messages to be displayed in response to the progress of imaging include, for example, "PET imaging will be started", "imaging will take about 30 minutes", "the remaining time for imaging is 10 minutes", or "PET imaging has been completed". Therefore, the subject P can recognize the progress of imaging by viewing these messages, and can be imaged without feeling anxiety or a sense of being enclosed. Needless to say, time may be displayed using an analog or digital indicator, etc., rather being displayed in a string of letters.

Furthermore, if the surface of the dome bar 14 in the imaging part 13 is made available as a screen, it can make the subject P relaxed and reduce anxiety, as well as continue imaging while preventing boredom, even during imaging that takes a long time, by controlling a projector arranged outside of the front cover 11 or rear cover 12 of the medical image diagnostic device unit 10 with the navigation controller 80 and projecting not only the progress of imaging but also a video depending on the preferences of the subject P.

As described above, according to the present invention, even if the field of view of the subject P is limited to the narrow imaging part 13 extending in a tubular manner, the subject P is able to view the information displayed on the display part 40 in the imaging part 13 so that it may contribute to relieve the sense of being enclosed, or the anxiety of the subject P.

It should be noted that the present invention need not be limited to the examples described above but may be executed in a variety of aspects. For example, without limitation to a combination of an X-ray CT device and a PET device, the present invention may be applied to the X-ray CT device and the PET device individually, and the medical image diagnostic device may be a magnetic resonance imaging device. However, the display part or the illumination part provided in the imaging part of the magnetic resonance imaging device need to be formed from non-magnetic materials.

What is claimed is:

1. A medical image diagnostic device with a tubular space for inserting an object into its interior, wherein the medical image diagnostic device comprises:
    an X-ray imaging detector configured to detect X-rays emitted from said object, and disposed at locations along the direction of the circumference, which are areas in the longitudinal direction of said tubular space and represent a cross-section of said tubular space;
    a radiation detector configured to detect radiation emitted from said object, and disposed at locations along the direction of the circumference, which are areas different from said X-ray imaging detector of said tubular space and represent a cross-section of said tubular space; and
    a display part that shows information intended for said object, disposed at locations allowing a light emission range of light emitted by the display part to be between said X-ray imaging detector and said radiation detector, and that are areas in the longitudinal direction of said tubular space,
    wherein said display part is disposed within the upper part of the circumference representing a cross-section of said tubular space, when said medical image diagnostic device is installed, and is disposed between said radiation detector and said X-ray imaging detector.

2. The medical image diagnostic device recited in claim 1, wherein said display part, on the upper part of the circumference representing a cross-section of said tubular space, comprises a first display part that is disposed between said radiation detector and the exterior of said medical image diagnostic device, and a second display part that is disposed between said radiation detector and said X-ray imaging detector.

3. A medical image diagnostic device with a tubular space for inserting an object into its interior, wherein the medical image diagnostic device comprises:
    an X-ray imaging detector configured to detect X-rays emitted from said object, and disposed at locations along the direction of the circumference, which are areas in the longitudinal direction of said tubular space and represent a cross-section of said tubular space;
    a radiation detector configured to detect radiation emitted from said object, and disposed at locations along the direction of the circumference, which are areas different from said X-ray imaging detector of said tubular space and represent a cross-section of said tubular space; and
    a light emitting part configured to illuminate said tubular space, said light emitting part being disposed at locations to set a light emission range to be at the exteriors of said X-ray imaging detector and said radiation detector, and that are areas in the longitudinal direction of said tubular space,
    wherein said light emitting part comprises an illumination part, and wherein said illumination part is disposed on the lower part of the circumference representing a cross-section of said tubular space, when said medical image diagnostic device is installed.

4. The medical image diagnostic device recited in claim 3, wherein said illumination part is disposed within the lower part of the circumference representing a cross-section of said tubular space, said disposition being between said radiation detector and the exterior of said medical image diagnostic device, and/or between said radiation detector and said X-ray imaging detector.

5. The medical image diagnostic device recited in claim 3, wherein said illumination part, on the lower part of the circumference representing a cross-section of said tubular space, comprises a first illumination part that is disposed between said radiation detector and the exterior of said medical image diagnostic device, and a second display part that is disposed between said radiation detector and said X-ray imaging detector.

6. A medical image diagnostic device with a tubular space for inserting an object into its interior, wherein the medical image diagnostic device comprises:
    an X-ray imaging detector configured to detect X-rays emitted from said object, and disposed at locations along the direction of the circumference, which are areas in the longitudinal direction of said tubular space and represent a cross-section of said tubular space;
    a radiation detector configured to detect radiation emitted from said object, and disposed at locations along the direction of the circumference, which are areas different from said X-ray imaging detector of said tubular space and represent a cross-section of said tubular space; and
    a light emitting part configured to illuminate said tubular space, said light emitting part being disposed at locations to set the light emission range to be at the exteriors of said X-ray imaging detector and said radiation detector, and that are areas in the longitudinal direction of said tubular space,
    wherein said light emitting part comprises shielded parts on both sides of the longitudinal direction of said tubular space, said shielded parts being configured to guide the light from said light emitting part to the exterior of said X-ray imaging detector and said radiation detector.

* * * * *